United States Patent
Barzilay et al.

(10) Patent No.: US 7,993,331 B2
(45) Date of Patent: Aug. 9, 2011

(54) METHOD AND DEVICE FOR REMOVING HAIR

(75) Inventors: Amir Barzilay, Zur Hadassah (IL); Alon Goren, Moshav Ben-Shemen (IL); Abraham Dayan, Bat Yam (IL); Vladimir Furman, Ashkelon (IL); Assaf Guterman, Tel-Aviv (IL); Yehuda Niv, Nes Ziona (IL)

(73) Assignee: Applisonix Ltd., Rechovot (IL)

( * ) Notice: Subject to any disclaimer, the term of this patent is extended or adjusted under 35 U.S.C. 154(b) by 1132 days.

(21) Appl. No.: 10/590,477

(22) PCT Filed: Feb. 20, 2005

(86) PCT No.: PCT/IL2005/000210
§ 371 (c)(1), (2), (4) Date: Aug. 24, 2006

(87) PCT Pub. No.: WO2005/079687
PCT Pub. Date: Sep. 1, 2005

(65) Prior Publication Data
US 2007/0173746 A1    Jul. 26, 2007

Related U.S. Application Data

(60) Provisional application No. 60/546,956, filed on Feb. 24, 2004.

(51) Int. Cl.
*A61B 18/00* (2006.01)
*A61B 18/04* (2006.01)

(52) U.S. Cl. .............................. 606/27; 601/2

(58) Field of Classification Search .......... 601/2; 606/9, 606/27
See application file for complete search history.

(56) References Cited

U.S. PATENT DOCUMENTS

| | | |
|---|---|---|
| 5,143,063 A | 9/1992 | Fellner |
| 5,522,814 A | 6/1996 | Bernaz |
| 6,090,101 A | 7/2000 | Quon et al. |
| 6,200,326 B1 | 3/2001 | Narayanan et al. |
| 6,267,771 B1 | 7/2001 | Tankovich et al. |
| 6,544,259 B1 | 4/2003 | Tsaliovich |
| 6,685,927 B2 | 2/2004 | Sumian et al. |
| 2002/0055693 A1 | 5/2002 | Thompson et al. |
| 2002/0165529 A1 | 11/2002 | Danek |
| 2003/0212351 A1* | 11/2003 | Hissong et al. .......... 601/2 |
| 2005/0154332 A1* | 7/2005 | Zanelli et al. .......... 601/2 |
| 2007/0239079 A1* | 10/2007 | Manstein et al. ........ 601/2 |

(Continued)

FOREIGN PATENT DOCUMENTS
EP    0573618    8/1995
(Continued)

OTHER PUBLICATIONS

Communication Pursuant to Article 94(3) EPC Dated Feb. 12, 2009 From the European Patent Office Re.: Application No. 05709110.0.

(Continued)

*Primary Examiner* — Roy D Gibson
*Assistant Examiner* — Kaitlyn E Helling (57) ABSTRACT

A method of treating unwanted hair is disclosed. The method comprises: transmitting acoustic waves through the hair so as to generate heat at a follicle, a dermal papilla, a hair bulge and/or a germinal matrix of the hair. The heat itself is sufficient to damage or destroy the follicle, the dermal papilla, the hair bulge and/or the germinal matrix.

27 Claims, 6 Drawing Sheets
(2 of 6 Drawing Sheet(s) Filed in Color)

U.S. PATENT DOCUMENTS

| | | | |
|---|---|---|---|
| 2008/0154157 A1* | 6/2008 | Altshuler et al. | 601/2 |
| 2008/0183110 A1* | 7/2008 | Davenport et al. | 601/3 |
| 2008/0195000 A1* | 8/2008 | Spooner et al. | 601/2 |
| 2009/0171253 A1* | 7/2009 | Davenport | 601/2 |
| 2009/0248448 A1* | 10/2009 | Zakay et al. | 705/3 |

FOREIGN PATENT DOCUMENTS

| | | |
|---|---|---|
| GB | 2384674 | 7/2003 |
| JP | 02279107 | 11/1990 |
| JP | 08154728 | 6/1996 |
| JP | 01029126 | 6/2001 |
| JP | 2002-527162 | 8/2002 |
| WO | WO 99/29245 | 6/1999 |
| WO | WO 00/21612 | 4/2000 |
| WO | WO 01/13757 | 1/2001 |
| WO | WO 01/26735 | 4/2001 |
| WO | WO 01/33991 | 5/2001 |
| WO | WO 0209813 A1 * | 2/2002 |
| WO | WO 02/09813 | 7/2002 |
| WO | WO 03/065347 | 7/2003 |

OTHER PUBLICATIONS

Communication Relating to the Results of the Partial International Search Dated Jul. 4, 2005 From the International Searching Authority Re.: Application No. PCT/IL2005/000210.

International Report on Patentability Dated Jul. 3, 2006 From the International Preliminary Examining Authority Re.: Application No. PCT/IL2005/000210.

International Search Report Dated Oct. 28, 2005 From the International Searching Authority Re.: Application No. PCT/IL2005/000210.

Translation of Office Action Dated May 23, 2008 From the Patent Office of the People's Republic of China Re.: Application No. 200580011895.8.

Written Opinion Dated Oct. 28, 2005 From the International Searching Authority Re.: Application No. PCT/IL2005/000210.

Written Opinion Dated Mar. 29, 2006 From the International Preliminary Examining Authority Re.: Application No. PCT/IL2005/000210.

Office Action Dated Jul. 13, 2009 From the Israeli Patent Office Re.: Application No. 177585 and Its Translation Into English.

Letter of Search for Prior Art Dated Oct. 27, 2004 From G. E. Ehrlich (1995) Ltd. Re.: File No. 28805.

Response Dated Mar. 7, 2010 to Office Action of Jan. 8, 2010 From the State Intellectual Property Office of the People's Republic of China Re.: Application No. 200580011895.8.

Response Dated Feb. 9, 2010 to Office Action of Jul. 13, 2009 From the Israel Patent Office Re.: Application No. 177585.

Translation of Office Action Dated Jan. 8, 2010 From the State Intellectual Property Office of the People's Republic of China Re.: Application No. 200580011895.8.

Translation of Notice of Reason for Rejection Dated Apr. 23, 2010 From the Japanese Patent Office Re.: Application No. 2007-500350.

* cited by examiner

METHOD AND DEVICE FOR REMOVING HAIR

RELATED APPLICATIONS

This application is a National Phase Application of PCT Patent Application No. PCT/IL2005/000210 having International Filing Date of Feb. 20, 2005, which claims the benefit of U.S. Provisional Patent Application No. 60/546,956 filed on Feb. 24, 2004. The contents of the above Applications are all incorporated herein by reference.

FIELD AND BACKGROUND OF THE INVENTION

The present invention relates to aesthetic care and, more particularly, to a method and device for removing hair.

A hair is composed of a protein named keratin arranged in three layers, termed the outer cuticle; the middle cortex and the central medulla. Hair grows from a follicle, which is a small cup-shaped pit buried under the skin. The walls of the follicle form the outer root sheath of the hair. The base of the hair follicle, called the dermal papilla, is fed by the bloodstream which carries nourishment (e.g., nutrients and oxygen) to produce new hair and removes waste materials formed in the process (e.g., $CO_2$). The lower part of the follicle widens out to form a hair bulb containing a germinal matrix, which is the source of hair growth. Hair growth is initiated in the hair bulge, which is a small swell of the hair follicle that forms the attachment site of a small smooth muscle, called the arrector pili muscle. During the anagen phase (the growing phase of the hair), the dermal papilla sends signals to the stem cells in the hair bulge to migrate, downwards along the follicle. Triggered by the dermal papilla, the stem cells begin to proliferate and, following cell differentiation, a new hair shaft is formed.

Various methods and devices exist for removal of undesired hair [Hwang Liew, Dermatologic Surgery 25:6, June 1999, 431-439]. Known devices generally pluck hair affixed to a tissue using various types of gripping, pulling and/or cutting means. The existing techniques can be classified into two major categories: short-term and long-term hair removal techniques.

In short-hair removal techniques, the hair is removed without significantly damaging the biological regeneration and/or re-growth mechanisms found at the base of each hair. Such technique affects only that part of the hair shaft, which is located outside the skin, while the living part of the hair (in the hair follicle attached to dermal papilla) continues to grow. The most common short-term hair removal techniques include: shaving, rotary mechanical epilation, waxing and chemical depilation.

Shaving can cause nicks and cuts, and can leave a perception of an increase in the rate of hair re-growth. Shaving also can leave an undesirable stubble. Rotary mechanical epilation devices include a rotating pinching mechanism which pinches and pulls out the hairs in a rather painful manner.

Waxing, whilst taking out most of the hair adhered to wax and tearing apart the hair or disconnecting it from its follicle and papillae, leaves the papillae itself at least partially vital. Consequently, the living cells will establish a new hair germination zone subsequently leading to renewed hair growth. Waxing can leave hair papillae and skin pores sore and open to infection, and cannot be used in cases of varicose veins, moles or warts.

Chemical depilation, involves the use of high concentration of alkaline chemicals, usually calcium thioglycolate, that dissolve the protein structure of the hair, leading to its separation from the papillae. The chemical depilation is occasionally accompanied by skin irritation. Chemical depilation leaves the papillae itself at least partially vital, allowing regrowth of hair.

Conversely to the short-term hair removal techniques, long-term hair removal techniques affect the biological regrowth mechanisms of the removed hair, and thus have the potential of inhibiting re-growth of unwanted hair from the treated organ. The most common long-term hair removal techniques include: electrolysis, laser and intense pulsed (non-laser) light.

Electrolysis is performed by transmitting a direct current to the hair root in order to form hydroxyl ions that electrochemically destroy the germinative cells of the hair follicles. Electrolysis can also be performed using high frequency currents to heat the water of the hair follicle and to coagulate the germinative hair cells. Although, electrolysis is considered as a permanent method for hair removal, there is still a re-growth of 15-50% of the removed hair after treatment. Moreover, electrolysis utilizes the insertion of a needle into the hair follicle, which is a rather painful and infection-prone process. The results of this procedure heavily depend on the skill of the person operating the electrolysis device, and unskilled treatment may cause pigmentation, scarring of the skin, infection and small electrical shocks.

U.S. Pat. Nos. 5,632,741 and 5,752,948 disclose methods for hair removal by laser radiation. The hair follicle is irradiated by focused laser beam, resulting in a temperature rise and a destruction of the follicle. This technique, however, depends on individual hair color and achieves acceptable results mostly in cases where there is a combination of hair and light skin. For individuals having light hair, a carbon lotion can be applied prior to the irradiation so as to facilitate absorption of the laser energy, but this improvement does not provide satisfactory results. Even optimal candidates with dark hair and light skin suffer from 40-80% hair re-growth after 12 weeks. Moreover, the laser technique has severe side effects such as irritation, change of the skin pigmentation and some times scarring.

In the intense pulsed light method, filtered light energy is converted in the dermis to heat and absorbed by hair pigment to destroy the hair structures and impair hair re-growth This method has a much larger spot size than traditional laser technology, hence can cover the treatment area faster and in fewer sessions. On the other hand, in this method, larger areas of the skin are in danger of developing side effects such as thermal injury and pigmentation changes. Some extent of relief to the skin can be provided by extending the duration between successive pulses of light. However, long duration between pulses inevitably reduces the effectiveness of treatment because it also allows the hair follicle to cool.

U.S. Pat. No. 4,566,454 discloses the application of radiofrequency waves to the hair at a frequency selected such that the hair impedance to radiofrequency energy conduction is substantially lower than at other radiofrequency frequencies. Generally speaking, the main principles of this technique consist of finding and selecting a radiofrequency resonant frequency for a given hair to reduce its impedance, since the resonant frequency varies from hair to hair. Another technique, disclosed in U.S. Pat. No. 5,470,332, consists of a pre-treatment of the hair prior to applying electromagnetic energy thereto. This pre-treatment makes the hair more receptive to the electromagnetic energy prior to its reaching the root of the hair.

International Patent Application Nos. WO 01/13757 and WO 01/033991 disclose hair removal methods in which a hair to be removed is subjected to low frequency vibrations. The low frequency vibrations are transmitted to the hair root either through, the hair (WO 01/13757) or by irradiating a treatment zone (WO 01/0339913 and exert a force to cause the root to disconnect from the surrounding tissue. The disconnection is mainly due to relatively large vibration amplitude (tens of micrometers to a few millimeters, depending on the vibration generator) of the hair shaft. WO 01/13757 and WO 01/033991 recite a frequency range of four orders of magnitude (10 Hz to 100 kHz), but teach that the preferred vibration frequency is in the sub kilohertz range. There are two major drawbacks of this technique: first, the low frequency of the vibrations results in a poor absorption of energy by the hair shaft and generation of heat within the hair shaft; and second, the large vibration amplitude weaken the hair shaft and reduces its ability to effectively transmit waves to the hair root.

International Patent Application Publication No. WO 01/26735 discloses a technique for the removal of undesired hair by utilizing ultrasonic resonating waves at a treatment zone in a close proximity to the hair to be removed.

International Patent Application Publication No. WO 00/21612 discloses a technique for the removal of undesired hair by utilizing ultrasonic forces. The technique involves the production of a focused ultrasonic beam having an acoustic focal point in which the area of the beam is smallest and the intensity of the beam is the highest. The ultrasonic beam is irradiated through the skin, it penetrates through the skin layers above the hair papillae and its focal point reaches the papillae. The parameters of the beam are such that the intensity per unit area on the skin is sufficiently small not to damage the skin above the papillae, while at the focal point the ultrasonic energy is said to be high enough in order to destroy living cells. WO 00/21612 recites a three orders of magnitude range of ultrasound frequencies (20 kHz to 25 MHz), but teaches that the preferred ultrasound frequency is in the range of 3000 kHz to 7000 kHz. However, as such high frequencies are highly absorbed and poorly guided by the hair shaft material, the ultrasound waves have to be precisely directed onto the hair root. Any deviation of the focal point of the ultrasound beam from the hair root will result in an ineffective treatment and unnecessary pain to the subject. WO 00/21612 also teaches the application of ultrasound radiation using the hair shaft as a wave guide, for frequencies ranging generally from 1 MHz to 50 MHz and specifically from 15 MHz to 25 MHz. At such high ultrasound frequencies the rate of energy absorption by the hair shaft prohibits energy transport through the hair into the follicle. Additionally, WO 00/21612 teaches generation of cavitations within the hair root, by irradiating using ultrasound waves at a frequency range of 1 kHz to 5 MHz. The ultrasound waves are irradiating the hair root through the skin. Other embodiments are directed towards causing extraction of hair by resonance force and torque resulting in fatigue effects in the follicle, using ultrasound waves at a frequency range of 1 kHz to 5 MHz, preferably 2 MHz to 5 MHz.

International Patent Application Publication No. WO 02/09813 discloses a hair removal method in which the area from which the hair is to be removed is struck by ultrasonic waves until the temperature of the tissues is raised-as a result of the absorption of the energy carried by the ultrasonic wave-to a degree sufficient to cause damage to the hair follicle. Similarly to WO/0021612 as described hereinabove, WO 02/09813 teaches that the ultrasound waves should be focused, so as to obtain a focal spot with lateral dimensions of order of a few tenths of the millimeter and a longitudinal extension of a few millimeters. The small focal spot has to be precisely directed onto the follicle to cause the desired destruction.

International Patent Application Publication No. WO 03/065347 discloses a method of treatment of tissue by a focused beam of ultrasonic vibration. WO 03/065347 employs a plano-concave lens which focuses the ultrasonic vibration at the treatment zone.

U.S. Patent Application, Publication No. 2002/0165529 discloses a method of treating subcutaneous tissue to achieve a therapeutic effect of hair removal. The therapeutic effect can be achieved by delivery of ultrasound energy to subsurface tissue. Two or more ultrasound delivery elements are positioned in an array in a manner such that their resulting output constructively interferes and focused onto the desired subsurface location.

International Patent Application Publication No. WO 99/029245 discloses a method of permanents hair removal method that includes two treating steps. In a first step, ultrasound is used to introduce alkaline ions into the skin and around the hair follicles, and a second step potentiates the destructive chemical reaction between the alkaline ions and the hair follicles, using radiant energy in the visible region.

U.S. Pat. No. 6,544,259 discloses a hair removal method in which radio frequency radiation is applied to a selected skin zone so as to destroy the hair follicles. Subsequently, ultrasound waves are applied to the skin zone to shake up the hair with the destroyed follicle and thus slacken the union between the hair and the skin zone and underlying area. Once the union is slackened the hair is pulled out of the follicle.

U.S. Pat. No. 6,200,326 discloses a method and apparatus for long-term removal of hair by transmitting ultrasound energy to a needle passed through the skin into an individual hair follicle. The resulting cavitations within the area surrounding the hair follicle causes the hair follicle to be disrupted.

Additional prior art teaching the use of ultrasound for hair removal include Japanese Patent Nos. JP 2001029126 and JP 8154728.

The present invention provides solutions to the problems associated with prior art hair removal techniques.

SUMMARY OF THE INVENTION

The prior art fails to provide a hair removal method in which the transmission of acoustic waves through the hair shaft generate sufficient heat to destroy the hair root.

Although the prior art recites the use of acoustic waves for removal of unwanted hair, the prior art fails to provide a range of frequencies which is suitable to effect a transmission of acoustic waves through the hair shaft into the follicle.

Additionally the prior art fails to teach how to effectively couple the acoustic waves and the hair shaft so as to allow the transmission of the acoustic waves through the hair shaft.

Furthermore, the prior art fails to provide a hair removal method in which the transmission of acoustic waves through the hair shaft is improved by minimizing vibration of the hair haft.

It is therefore the object of the present invention to provide a method and device for hair removal via effective transmission of acoustic waves through the hair shaft at least into the follicle.

It is further the object of the present invention to provide a method and device for hair removal in which the acoustic waves generate sufficient heat to destroy the hair root.

It is further the object of the present invention to provide a method and device for hair removal in which the coupling between the hair shaft and the acoustic waves is enhanced.

It is further the object of the present invention to provide a method and device for hair removal in which the transmission of acoustic waves through the hair shaft is improved by minimizing vibration of the hair haft.

Thus, according to one aspect of the present invention there is provided a method of treating unwanted hair. The method comprises: transmitting acoustic waves through the hair so as to generate heat at a follicle, a dermal papilla, a hair bulge and/or a germinal matrix of the hair. According to a preferred embodiment of the present invention the heat is in itself sufficient to damage and/or destroy the follicle, the dermal papilla, the hair bulge and/or the germinal matrix.

According to another aspect of the present invention there is provided a method of treating unwanted hair. The method comprises gripping a segment of the hair and transmitting acoustic waves through the hair, wherein a length of the segment of the hair is selected so as to enhance an acoustic coupling between the hair and the acoustic waves.

According to an additional aspect of the present invention there is provided a method of treating unwanted hair. The method comprises transmitting acoustic waves through the hair wherein at least one of: a frequency, a power density and duration of transmission of the acoustic waves is selected so as to minimize vibrations of the hair.

According to further features in preferred embodiments of the invention described below, the frequency, power density and duration of transmission of the acoustic waves is selected so as to minimize longitudinal vibrations of the hair.

According to still another aspect of the present invention there is provided a method of treating unwanted hair. The method comprises transmitting acoustic waves at a frequency of from about 150 kHz to about 1300 kHz through the hair.

According to further features in preferred embodiments of the invention described below, the method further comprises using a wave condenser for condensing the acoustic waves, prior to the transmitting of the acoustic waves through the hair.

According to still further features in the described preferred embodiments the gripping comprises positioning the hair and/or the wave condenser such that a propagation direction of the acoustic waves while entering the wave condenser is generally parallel a longitudinal axis of the hair.

According to still further features in the described preferred embodiments the gripping comprise positioning the hair and/or the wave condenser such that a propagation direction of the acoustic waves while entering the wave condenser is generally perpendicular to a longitudinal axis of the hair.

According to still further features in the described preferred embodiments the gripping comprises positioning the hair and/or the wave condenser such that a propagation direction of the acoustic waves while entering the wave condenser is generally inclined to a longitudinal axis of the hair.

According to still further features in the described preferred embodiments the method further comprises gripping the hair prior to transmission of the acoustic waves so as to enhance acoustic coupling between the acoustic waves and the hair.

According to still further features in the described preferred embodiments the method further comprises pulling the hair so as to effect a detachment of the hair.

According to still further features in the described preferred embodiments the generation of the heat is such that the heat at the follicle, the dermal papilla, the hair bulge and/or the germinal matrix results in a temperature increment of at least 20 degrees centigrade, more preferably at least 30 degrees centigrade, most preferably at least 40 degrees centigrade.

According to still further features in the described preferred embodiments the acoustic waves comprise ultrasound waves.

According to still further features in the described preferred embodiments duration of transmission of the acoustic waves is less than about 5 seconds. According to still further features in the described preferred embodiments duration of transmission of the acoustic waves is less than about 1 second.

According to yet another aspect of the present invention there is provided a device for treating unwanted hair, the device comprises: a transducer for generating acoustic waves; and a wave condenser for condensing and transmitting the acoustic waves through the hair so as to generate heat at a follicle, a dermal papilla, a hair bulge and/or a germinal matrix of the hair; the heat being in itself sufficient to destroy the follicle, the dermal papilla, the hair bulge and/or the germinal matrix.

According to a further aspect of the present invention there is provided a device for treating unwanted hair, the device comprises: a transducer for generating acoustic waves; and a wave condenser for condensing and transmitting the acoustic waves through the hair, the wave condenser being designed and constructed to grip the hair along a segment of the hair, wherein the length of the segment is selected so as to enhance acoustic coupling between the hair and the acoustic waves.

According to still a further aspect of the present invention there is provided a device for treating unwanted hair, the device comprises: a transducer for generating acoustic waves and a wave condenser for condensing and transmitting the acoustic waves through the hair; wherein at least one of: a frequency, a power density and duration of transmission of the acoustic waves is selected so as to minimize vibrations of the hair. According to further features in preferred embodiments of the invention described below minimization is of longitudinal vibration.

According to yet a further aspect of the present invention there is provided a device for treating unwanted hair, the device comprises: a transducer for generating acoustic waves at a frequency of from about 150 kHz to about 1300 kHz; and a wave condenser for condensing and transmitting the acoustic waves through the hair.

According to further features in preferred embodiments of the invention described below, the wave condenser is designed and constructed such that a propagation direction of the acoustic waves while entering the wave condenser is generally parallel to a longitudinal axis of the hair.

According to still further features in the described preferred embodiments the wave condenser is designed and constructed such that the propagation direction of the acoustic waves while entering the wave condenser is generally perpendicular to the longitudinal axis of the hair.

According to still further features in the described preferred embodiments the wave condenser is designed and constructed such that the propagation direction of the acoustic waves while entering the wave condenser is generally inclined to the longitudinal axis of the hair.

According to still further features in the described preferred embodiments the wave condenser is designed and constructed to grip the hair so as to enhance acoustic coupling between the acoustic waves and the hair.

According to still further features in the described preferred embodiments the acoustic coupling is characterized by a coupling length selected such that the heat at the follicle, the dermal papilla, the hair bulge and/or the germinal matrix results in a temperature increment of at least 20 degrees centigrade.

According to still further features in the described preferred embodiments the coupling length is longer than about 1 mm. According to still further features in the described preferred embodiments the coupling length is shorter than about 6 mm.

According to still further features in the described preferred embodiments the transducer and the wave condenser are designed and constructed such the heat at the follicle, the dermal papilla, the hair bulge and/or the germinal matrix results in a temperature increment of at least 20 degrees centigrade.

According to still another features in the described preferred embodiments at least one of: a frequency, a power density and duration of transmission of the acoustic waves is select so as to minimize longitudinal vibrations of the hair.

According to still further features in the described preferred embodiments the frequency, the density and/or the duration of transmission of the acoustic waves is selected such that a characteristic amplitude of the longitudinal vibrations of the hair is below 10 micromoeters.

According to still further features in the described preferred embodiments the frequency is an off-resonance frequency.

According to still further features in the described preferred embodiments the transducer comprises a first part and a second part, where each of the first and second parts comprises at least one active element.

According to still further features in the described preferred embodiments the wave condenser comprises a first part coupled to the first part of the transducer, and a second part coupled to the second part of the transducer.

According to still further features in the described preferred embodiments the transducer is an ultrasound transducer generating ultrasound waves.

According to still further features in the described preferred embodiments the transducer comprises an active element selected from the group consisting of a piezoelectric ceramic element, and a piezoelectric composite element.

According to still further features in the described preferred embodiments the transducer comprises a planar active element.

According to still further features in the described preferred embodiments the transducer comprises a concaved active element.

According to still further features in the described preferred embodiments the transducer comprises a plurality of active elements arranged on a surface.

According to still further features in the described preferred embodiments the surface is a plane.

According to still further features in the described preferred embodiments the surface is a concaved surface.

According to still further features in the described preferred embodiments the device further comprises focusing element coupling the transducer and the wave condenser, the focusing element being designed and constructed to focus the acoustic waves into the wave condenser.

According to still further features in the described preferred embodiments each of the wave condenser and the focusing element comprises a first part and a second part, where the first and second parts of the focusing element respectively couple the first and second parts of the transducer and the first and second parts of the wave condenser.

According to still further features in the described preferred embodiments the focusing element comprises a tapered housing.

According to still further features in the described preferred embodiments a profile of the tapered housing is selected from the group consisting of a stepped profile, a linear profile, a segmented linear profile and an exponential profile.

According to still further features in the described preferred embodiments the device further comprises a plurality of focusing elements arranged such that each focusing element of the plurality of focusing elements is connected to one active element of the plurality of active elements and being designed and constructed to focus a respective portion of the acoustic waves into the wave condenser.

According to still further features in the described preferred embodiments the wave condenser comprises a chamber configured to receive the hair such that energy of the acoustic waves is transferred to the hair from a plurality of radial directions.

According to still further features in the described preferred embodiments the chamber contains an ultrasound transmission gel.

According to still further features in the described preferred embodiments the wave condenser comprises a surface characterized by a radius of curvature of from about 1 millimeter to about 10 millimeters.

According to still further features in the described preferred embodiments a shape of the surface is selected from the group consisting of a sphere, a cylinder, an ellipsoid, a paraboloid, a hyperboloid and any combination or portion thereof.

According still further features in the described preferred embodiments the wave condenser is operable to split thereby to form a gap for receiving the hair.

According to still further features in the described preferred embodiments the wave condenser and the transducer are operable to split thereby to form a gap for receiving the hair.

According to still further features in the described preferred embodiments the wave condenser and at least one of the transducer and the focusing element are operable to split thereby to form a gap for receiving the hair.

According to still further features in the described preferred embodiments the device further comprises a drive mechanism for imparting a motion of the wave condenser relative to the hair.

According to still further features in the described preferred embodiments the wave condenser is operable to periodically split and reassemble in a manner such that when the wave condenser splits, the hair engages the gap, and when the wave condenser is reassembled, the hair is gripped by the wave condenser and irradiated by the acoustic waves.

According to still further features in the described preferred embodiments the drive mechanism is configured to impart a rotary motion to the wave condenser.

According to still further features in the described preferred embodiments the drive mechanism is configured to impart a reciprocal linear motion to the wave condenser.

According to still further features in the described preferred embodiments the device further comprises a hair capturer, operatively associated with the wave condenser, for capturing the hair.

According to still further features in the described preferred embodiments the hair capturer is selected from the group consisting of a brush, a net and a clamp.

According to still further features in the described preferred embodiments the hair capturer is operable to lubricate the hair with an ultrasound transmission gel. According to still further features in the described preferred embodiments the device further comprises the ultrasound transmission gel.

According to still further features in the described preferred embodiments the hair capturer is operable to pull the hair so as to effect a detachment of the hair.

According to still further features in the described preferred embodiments the ultrasound waves a at a frequency of at least 150 kHz. According to still further features in the described preferred embodiments the ultrasound waves are at a frequency of at least 500 kHz.

According to still further features in the described preferred embodiments the ultrasound waves are at a frequency range of from about 150 kHz to about 1300 kHz. According to still further features in the described preferred embodiments the ultrasound waves are at a frequency range of from about 500 kHz to about 1000 kHz.

According to still further features in the described preferred embodiments the transducer is configured to generate the acoustic waves at a power density of at least 1 watt per square centimeter, more preferably from about 1 watt per square centimeter to about 100 watts per square centimeter.

The present invention successfully addresses the shortcomings of the presently known configurations by providing a method and device for removing hair, which enjoy properties far exceeding the prior art.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The file of this patent contains at least one drawing executed in color photograph. Copies of this patent with color photograph(s) will be provided by the Patent and Trademark Office upon request and payment of necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

The present invention is of a method and device which can be used for treating unwanted hair or hairs. Specifically, the present invention can be used to destroy hair roots so as to prevent, temporarily or permanently, re-growth of hairs therefrom. The present invention can further be used to remove hair from hair covered surfaces designated for hair removal.

The principles and operation of a method and device according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 1:
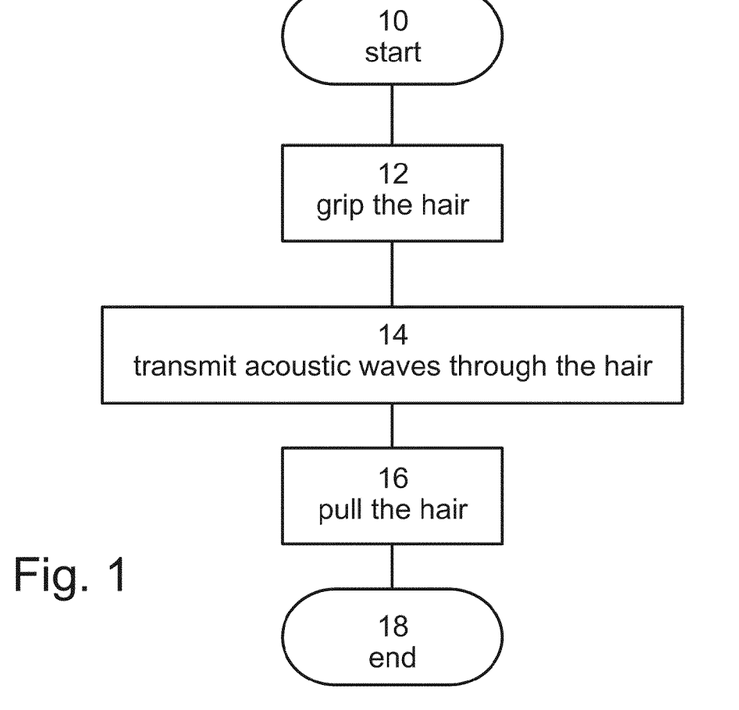
FIG. 1 is a flowchart of a method for treating unwanted hair, according to various exemplary embodiments of the invention.

Referring now to the drawings, FIG. 1 is a flowchart of a method for treating unwanted hair, according to a preferred embodiment of the present invention. It is to be understood that unless otherwise defined, the method steps described hereinbelow can be executed either contemporaneously or sequentially in many combinations or orders of execution. Specifically, neither the ordering nor the numerals of the flowchart of FIG. 1 are to be considered as limiting. For example, two or more method steps, appearing in the following description or in the flowchart of FIG. 1 in a particular order, can be executed in a different order (e.g., a reverse order) or substantially contemporaneously.

The method starts in step 10 and, optionally and preferably, continues to step 12 in which the hair is gripped or captured. The gripping/capturing is for the purpose of enhancing acoustic coupling between the hair and acoustic waves transmitted therethrough in a later step (see step 14 below), and can be done using any device known in the art, e.g., a brush, a net, a clamp and the like.

The method continues to step 14 in which acoustic waves, e.g., ultrasound waves, are transmitted through the hair. As demonstrated in the Examples section that follows, the energy carried by the acoustic waves can be delivered to the hair root through the hair shaft itself, which in various exemplary embodiments of the present invention serves as an acoustic waveguide. The propagation of the acoustic waves through the hair is the result of instantaneous movement of particles along the direction of the hair, leading to a wave of local compression and tension stresses propagating in parallel to the hair's longitudinal axis.

Step 14 is preferably executed such that a sufficient amount of heat is generated at the follicle, dermal papilla, hair bulge and/or germinal matrix of the hair. The heat by itself is preferably sufficient to destroy the follicle, dermal papilla, hair bulge and/or germinal matrix.

The transmission of acoustic waves according to the teachings of WO 01/26735 is insufficient to destroy or damage tissue in the follicle. In sharp distinction, as further demonstrated in the Example section that follows, the present invention successfully causes damage or destruction at hair root tissue.

As used herein, destruction refers to hyperthermia, necrosis and/or any other damage to the cells in the follicle (dermal papilla, hair bulge, germinal matrix, etc.) which, at least temporarily, preferably permanently prevents the re-growth of the hair. The prevention of re-growth is preferably for a prolonged period of time, for example, for more than a month, preferably for more than six months, more preferably for more than a year, most preferably permanently.

According to a preferred embodiment of the present invention the generated heat results in a temperature. increment of at least 20° C., more preferably at least 30° C., most preferably at least 40° C. Such heat in itself is sufficient to at least temporarily, preferably permanently destroy or at least damage the follicle, dermal papilla, hair bulge and/or germinal matrix. It is recognized that when the temperature of the soft tissue present in the follicle reaches high levels for a sufficient duration, a phenomenon known as "protein denaturing" can occur, resulting in a necrosis of the tissue.

By utilizing the hair as a waveguide of acoustic energy, the present embodiments are minimally sensitive and/or fully insensitive to several physiological parameters of the treated person include, without limitation, skin color tone, hair color tone and level of contrast between skin color tone and hair color tone. Prior art hair removal techniques making use of other energy types (e.g., light, laser, electromagnetic radiation, radiofrequency radiation, X-ray radiation) are significantly sensitive to such color tone parameters. Thus, the present embodiments have the advantage of treating significantly larger populations comparing with such other hair removal techniques. Without limitation, the present embodiments are suitable for individuals with dark skin tone, individuals with very light hair tone, and individuals with minimal amount of melanin in the hair.

The present embodiments take advantage of the proximity of the dermal papilla, hair bulge and germinal matrix to the hair shaft. In particular, this proximity is exploited during the hair Anagen growth phase, whereby acoustic energy transmitted through the hair shaft as a waveguide, is converted into thermal energy in the follicle, dermal papilla, hair bulge and germinal matrix. When integrated within the hair base, and taking into account the very small volume of the dermal papilla, hair bulge and germinal matrix (several hundreds of cubic microns), a rapid and short increase in the temperature as a result of absorption of acoustic energy, timely elevates the generation of sufficient thermal effects, sufficient enough to cause the desired destruction of cells. Preferably, the thermal effects are sufficiently short in their duration, so as to selectively destroy the follicle, germinal matrix, hair bulge and/or dermal papilla, with minimal or no damage to other soft biological tissues surrounding the follicle or hair shaft. As will be appreciated by one ordinarily skilled in the art, the combination of short duration and use of the hair shaft as an acoustic waveguide allows the selective damage to the cells in the follicle substantially without damaging other important tissues and sub-organs surrounding the hair shaft and bulb.

The parameters of the acoustic waves may be adapted according to one or more of the following physiological parameters characterizing the person and/or body organ being treated: hair growth phase (Anagen, Catagen or Telogen), depth of the hair base under the skin, distance between hair base and papilla, total hair length (under and above the skin hair), coupling angle, hair color, hair diameter, force required to detach a vital untreated hair from vital untreated hair base, force required to detach a hair from a partially treated hair base, and force required to detach a hair from fully treated and materially destroyed hair base.

Once the aforementioned cells are destroyed, the method, optionally and preferably continues to step 16 in which the hair is pulled so as to effect a detachment of the hair. The pulling is preferably done so as to detach the hair shaft from the follicle, or, more preferably, to detach the hair shaft and its inner root sheath from the follicle.

According to a preferred embodiment of the present invention the transmission of acoustic waves is done in a manner such that the acoustic waves impinge on a particular segment of hair, interact with that particular segment and propagate through the hair such that hair serves as an acoustic waveguide. In various exemplary embodiments of the invention the acoustic coupling between the acoustic waves and the hair is not point-like coupling. The acoustic coupling is preferably characterized by a predetermined coupling length, h, which can be, for example, the length of the particular segment onto which the acoustic waves impinge. The coupling length can be defined, for example, in the gripping step, whereby gripping a longer portion of the hair shaft corresponds to a longer coupling length.

As will be appreciated by one ordinarily skilled in the art, the coupling length correlates with amount of energy (in the form of acoustic waves) transferred to the hair shaft. It was found by the Inventors of the present invention (see FIG. 10 in the Examples section that follows) that the temperature increment at the tissue of the follicle directly depends on the coupling length.

Thus, in sharp distinction to the prior art (see, e.g., International Patent Application Nos. WO 00/21612 and WO 02/09813), where focused ultrasound beam is directed, substantially to a point, the present embodiment employ a non point-like coupling.

Thus, according to a preferred embodiment of the present invention the coupling length h is selected such that the generated heat results in a temperature increment of 20-40° C., which is preferably achieved by a coupling length of above 1 mm, more preferably above 2 mm. In various exemplary embodiments of the invention the coupling length is below 6 mm. A typical value for the coupling length is about 5 mm.

As used herein the term "about" refers to ±10%.

When acoustic waves interact with matter, the energy carried by the waves can be absorbed by, reflected off, or transmitted through the matter. The ability of a waveguide to transmit waves is commonly characterized by a transmission coefficient, which corresponds to the fraction of energy being successfully transmitted through the waveguide, without being absorbed or reflected. As the treatment of the hair is essentially by guiding the acoustic waves through the hair shaft, the effectiveness of the treatment depends on the transmission coefficient of the hair shaft, where larger transmission coefficient corresponds to better efficiency of energy transfer through the hair shaft to the cells in the follicle.

It is known that when acoustic waves interact with an object (a hair shaft in the present case), the object starts to vibrate at amplitude which depends on the frequency of the acoustic waves and natural frequency of the object (the natural frequency of the object depends on many parameters of the object, including, material, structure, geometry and the like). The acoustic waves serve as a time-dependent external force acting on the object and compensating the energy lose of the object to the environment. The response, of the object to the interaction with the acoustic waves is typically described using a frequency response curve, which is a graph representing the vibration amplitude of the object as a function of the frequency. A particular case in which the frequency of the acoustic waves equals the natural frequency of the object is called a resonance. Typically, at the resonance, the response curve has a sharp peak near the resonance frequency.

It was found by the Inventors of the present invention that longitudinal vibration of the hair shaft significantly decreases the ability of the hair to transmit energy to the follicle. Longitudinal vibrations of the hair, besides weakening the hair's strength, damp the compression and tension stress along the hair, and, consequently, decrease its transmission ability. When the amplitude of the longitudinal vibration is extremely large (e.g., as in the cases of vibrations at, or close to, the resonance frequency), the hair shaft may collapse and completely loose it ability to transmit the energy to the follicle.

Additionally, too large longitudinal vibrations of the hair shaft may lead to generation of transverse vibrations. Although being smaller in amplitude, relatively to the longitudinal vibrations, it is recognized that transverse vibrations of the hair shaft are very problematic because transverse vibrations contribute to loss of energy to the tissue surrounding the hair shaft before it reaches the root. A byproduct of such. energy loss is the delivery of energy in the form of heat to tissue surrounding the hair shaft.

Thus, according to a preferred embodiment of the present invention, the frequency, power density and/or duration of the acoustic waves is selected so as to minimize vibrations of the hair. Such minimization can include the minimization of longitudinal and/or transverse vibrations. Preferably, the above acoustic waves parameters are selected so as to minimize longitudinal vibrations. Most preferably, the longitudinal vibrations are minimized such that the transverse vibration are inherently reduced. This embodiment is in sharp distinction to the prior art in which the general trend is to generate large longitudinal vibrations in the hair shaft (see, for example, International Patent Application Nos. WO 01/13757 and WO 01/033991, where vibrations of at least tens of micrometers are used).

The characteristic amplitude of the longitudinal vibrations of the hair is preferably below 10 μm, more preferably below 5 μm most preferably below 1 μm. Small longitudinal vibrations can be achieved by selecting an off-resonance frequency for the acoustic waves.

It was found by the Inventors of the present invention that energy absorption by the hair shaft at low ultrasound frequencies is quite poor, and no effective heating of the follicle can be attained without causing overheating and damage to a large volume of tissue around the hair shaft and the follicle. On the other hand, at high ultrasound frequencies there is a high level of energy absorption by the hair shaft leading to overheating of the hair shaft such that the hair shaft is damaged, destroyed and/or broken and no effective transmission of energy to the follicle can be sustained.

As stated in the Background section above, several prior art documents (see, e.g., International Patent Nos. WO 01/13757, WO 01/033991 and WO 00/21612), recites extremely wide frequency ranges (3-4 orders of magnitude), which inevitably include both low frequencies for which there is an insufficient level of heating efficiency of the follicle due to low absorption, and high frequencies for which there is an insufficient level of transmission efficiency to the follicle due to over-absorption. According to a preferred embodiment of the present invention the frequency is selected to allow optimal transmission of the acoustic waves to and energy absorption by the follicle. According to a preferred embodiment of the present invention the frequency is a least 150 kHz or, more preferably at least 500 kHz. Typical frequency ranges include, without limitation from about 150 kHz to about 1300 kHz, and from about 500 kHz to about 1000 kHz. When the hair shaft is supplemented by reinforcing chemical additives, the frequency can be larger than 1300 kHz.

In various exemplary embodiments of the invention the duration of transmission of the acoustic waves is less than 5 seconds, in other preferred embodiments the duration is less than 1 second, say about 10-100 milliseconds. As stated, the heat generated in the soft tissue of the hair follicle results in a temperature increment which is sufficient to cause the aforementioned damage or destruction. As further explained in the Examples section that follows, absorption of a few milliwatts of power in the hair bulb can increase the temperature to the desired level. Thus, in various exemplary embodiments of the present invention, the acoustic waves are generated at a power density selected such that the absorbed power in the hair bulb is at least 1 milliwatt, preferably, but not obligatorily, not exceeding about 10 milliwatts. In various exemplary embodiments of the invention the desired absorbed power in the hair bulb is achieved using an acoustic wave transducer operating at a power density of from about 1 watt per square centimeter to about 100 watts per square centimeter, say, a few watts per square centimeter.

Figure 2:
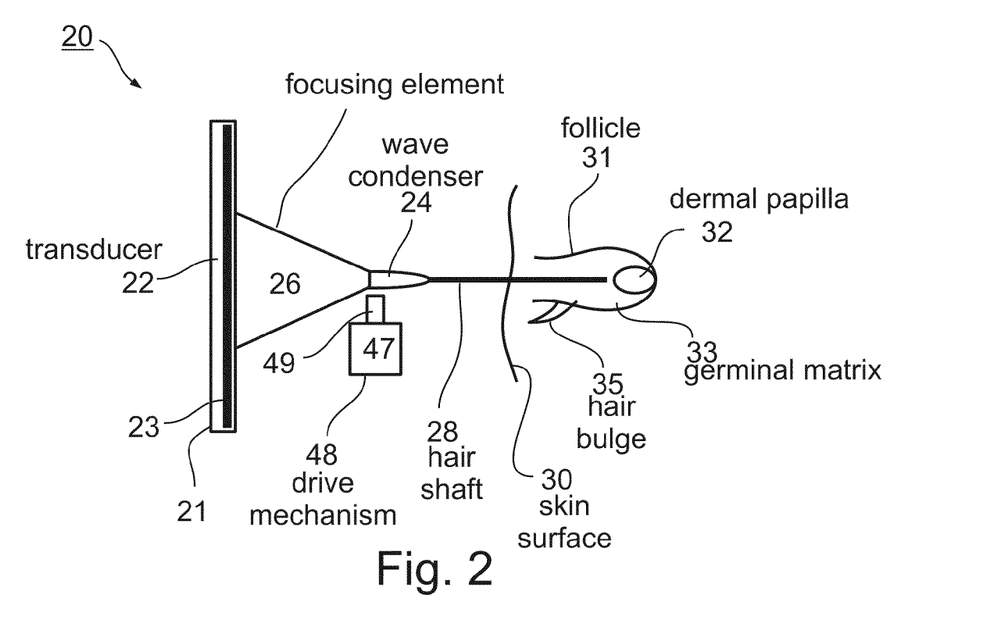
FIG. 2 is a schematic illustration of a device for treating unwanted hair, according to various exemplary embodiments of the invention.

Reference is now made to FIG. 2 which is a schematic illustration of a device 20 which can be used for treating unwanted hair, e.g., by executing one or more of the above method steps. Device 20 preferably comprises a transducer 22, for generating the acoustic waves, and a wave condenser 24 for condensing and transmitting the acoustic waves through the hair. The acoustic waves propagate through the hair shaft 28 past the skin surface 30 and generate a sufficient amount of heat at the follicle 31, dermal papilla 32, hair bulge 35 and/or germinal matrix 33, so as to cause damage to the tissue and/or destruction thereof.

Transducer 22 preferably comprises an active element 23 which can be a piezoelectric ceramic element or a piezoelectric composite element. The active element can be planar or non-planar (e.g., concaved), a single element or an arrangement of a plurality of elements on a suitable planar or non-planar surface. The back side of transducer 22 (designated in FIG. 2 by numeral 21) is preferably exposed to air so as to minimize loss of ultrasound energy: a substantial part of the ultrasound energy is reflected from the air-piezoelectric material interface back into the piezoelectric element. Alternatively, back side 21 can be sealed, e.g. using a polymeric foam, such as polystyrene, which provides boundary characteristics similar to those of air.

According to a preferred embodiment of the present invention wave condenser 24 is designed and constructed to establish the aforementioned acoustic coupling between the hair and the acoustic waves. Preferably, wave condenser 24 grips the hair so as to establish the desired acoustic coupling. Different coupling lengths can be established by allowing different gripping depths of wave condenser 24.

Besides depending on the coupling length, the acoustic coupling also depends on the orientation of the hair shaft, e.g., relative to the main propagation direction of the acoustic waves while entering wave condenser 24. It was found by the Inventors of the present invention that an effective transmission of energy through the hair can be achieved when the propagation direction of the acoustic waves while entering wave condenser 24 is generally parallel to the longitudinal axis of the hair shaft. This embodiment is referred to hereinunder as the "parallel orientation embodiment".

Other, non parallel orientations of the hair shaft are also contemplated. For example, in another preferred embodiment of the present invention the propagation direction of the acoustic waves while entering wave condenser 24 is generally perpendicular to the longitudinal axis of the hair shaft. This embodiment is referred to hereinunder as the "perpendicular orientation embodiment".

In an additional embodiment of the present invention, the propagation direction of the acoustic waves while entering wave condenser 24 is generally a at a predetermined angle, other than 0° or 90°, to the longitudinal axis of the hair shaft. This embodiment is referred to hereinunder as the "inclined orientation embodiment". As will be appreciated by one of ordinary skills in the art, the inclined orientation embodiment is a linear combination between the parallel and perpendicular orientation embodiments. Representative examples of inclination angles include, without limitation, about 10°, 20°, 30°, 40°, 50°, 60°, 70° and 80°.

In various exemplary embodiments of the present invention, the shape of wave condenser 24 is selected in accordance with the desired orientation embodiment. Yet, a given design of wave condenser 24, does not necessarily limits the use of device 20 to a particular orientation embodiment. For example, when wave condenser 24 is designed and constructed for the parallel orientation embodiment, the hair shaft can be positioned in or close to wave condenser 24, in any orientation (parallel, perpendicular, inclined). Similarly, any orientation of the hair shaft can be employed when wave condenser 24 is designed and constructed for the perpendicular orientation embodiment.

Figures 3A, 3B:
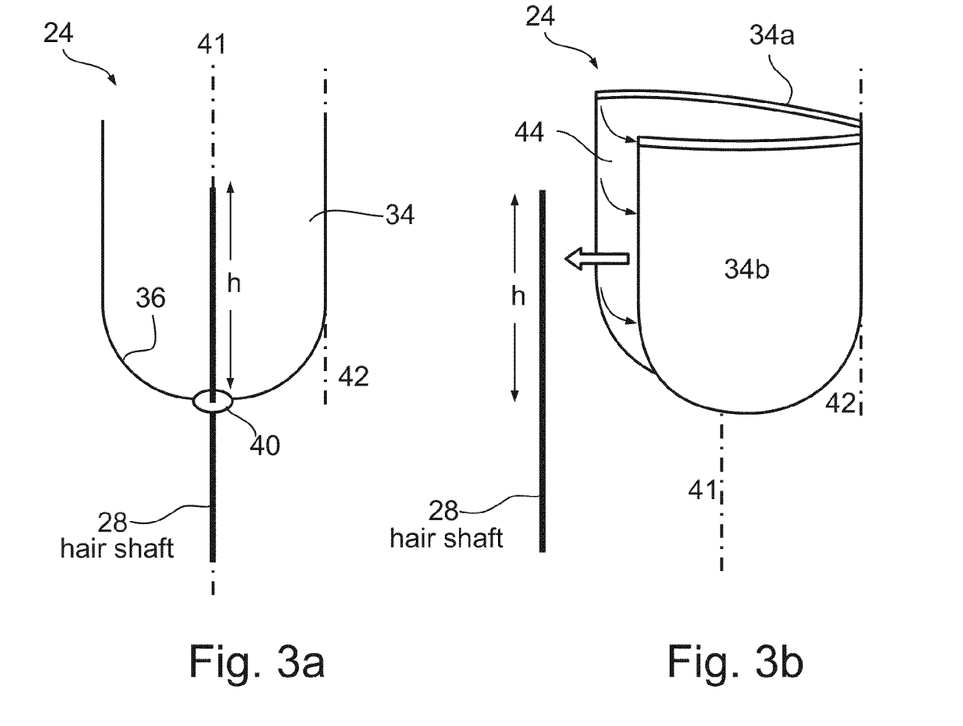
FIGS. 3a-b are schematic illustrations of a wave condenser, in a preferred embodiment in which the propagation direction of the acoustic waves, while entering the wave condenser is generally parallel to a longitudinal axis of the hair.

FIGS. 3a-b are schematic illustrations of a particular configuration of wave condenser 24, which is preferably used in the parallel orientation embodiment. Condenser 24 preferable comprises a chamber 34 which receives hair shaft 28. Chamber 34 can be filled with an ultrasound transmission gel for the purpose of impedance matching and enhancement of acoustic coupling. The acoustic waves generated by transducer 22 (not shown in FIG. 3) are reflected from the inner side of surface 36 of chamber 34 and the energy carried by the waves is therefore entrapped in chamber 34. Hair shaft 28 is introduced into chamber 34 to form coupling length, h, (a few millimeters, as stated) between the acoustic waves and hair shaft 28. While bouncing back and forth off surface 36, the acoustic waves are transferred into hair shaft 28 from a plurality of directions, more preferably from substantially all radial directions (360°). Thus, condenser 24 allows the acoustic waves to envelope a segment of the hair and not to focus on a single point of the hair. As will be appreciated by one of ordinary skill in the art, such configuration facilitates the acoustic coupling between the hair and the acoustic waves.

Surface 36 can have any shape which allows the reflection of the acoustic waves and the acoustic coupling with hair shaft 28. Preferably, surface 36 is non-planar with a characteristic radius of curvature of from about 1 mm to about 10 millimeters, more preferably between about 2 mm and about 5 mm. Representative examples of surface shapes include, without limitation, a sphere, a cylinder, an ellipsoid, a paraboloid, a hyperboloid and any combination or portion thereof. In the exemplary embodiment shown in FIGS. 3a-b surface 36 comprises a cylinder with a hemisphere head.

There is more than one configuration which is contemplated to allow wave condenser 24 to grip or capture hair shaft 28. In one embodiment, shown in FIG. 3a, hair shaft 28 is introduced through a hole 40 into chamber 34. In another embodiment, shown in FIG. 3b, chamber 34 momentarily splits, e.g., about an axis 42, into two parts (designated 34a and 34b in FIG. 3b) defining a gap 44, captures hair shaft 28 in gap 44 and reassembled on hair shaft 28. When transducer 22 is adhered to condenser 24, both transducer 22 and condenser 24 preferably split and reassembled together (see, e.g., FIGS. 4a-b and the accompanying description below). Parts 34a and 34b can be disengaged either by rotary motion thereof about axis 42 or by any other motion, e.g., a linear motion in a perpendicular, parallel or at any other direction relative to axis 42. For example, in an alternative, yet preferred embodiment, there is a complete detachment of part 34a from part 34b to enable the insertion of hair shaft 28 to gap 44. In still another preferred embodiment parts 34a and 34b slide one relative to the other to capture hair shaft 28 therebetween. Parts 34a and 34b are preferably, but not obligatorily symmetric to each other (e.g., two halves of a cylinder).

In any of the above configurations, the chamber or its two parts can be partly hollow and filled with ultrasound gel. The chamber or its two parts can be made of any suitable material, such as, but not limited to, metal (e.g., aluminum), polymer (e.g., Room Temperature Vulcanizing rubber, abbreviated to RTV) or combination thereof. Whether chamber contains ultrasound gel, the acoustic contact between the wave condenser parts and the hair shaft can be further improved by applying ultrasound gel to the hair shaft or to the surfaces of the wave condenser contacting the hair shaft prior to the activation of the transducer.

According to a preferred embodiment of the present invention, the location of hair shaft 28 within wave condenser 24 is along or close to its symmetry axis (designated 41 in FIGS. 3a-b). The advantage of this embodiment is that the positioning of the hair along the symmetry axis enhances the efficiency of energy transfer to the hair shaft, because constructive interference of acoustic waves makes the density of energy along the symmetry axis significantly larger than in other locations in chamber 34. For non-axially-symmetric shapes of chamber 34 the preferred location of hair shaft is close to the center of chamber 34.

Referring now again to FIG. 2, device 20 preferably comprises a focusing element 26, coupling between transducer 22 and wave condenser 24. Focusing element 26 focuses the acoustic waves by making the beam of acoustic waves converge toward an area of space located in wave condenser 24. Focusing element 26 is preferably attached to transducer 22, such that there is good transmission of acoustic waves from transducer 22 and element 26. This can be achieved using any adhesive known in the art.

In the embodiments in which, the hair shaft is captured by momentary splitting of condenser 24 (see FIG. 3*b*), focusing element 26 and/or transducer 22 preferably split together with condenser 24 (see, e.g., FIGS. 4*a-b* and the accompanying description below). Once a length h of hair shaft 28 enters gap 44, the splitting parts reassemble and, while hair shaft 28 is gripped inside chamber 34, transducer 22 is activated to generate the acoustic waves. Focused by focusing element 26, the waves enter condenser 24, couple with hair shaft 28 and propagate through hair shaft 28, preferably with minimal (and transverse) vibrations, toward follicle 31. Upon reaching soft tissue cells in follicle 31 (dermal papilla 32, hair bulge 35 and/or germinal matrix 33), the energy, carried by the waves in the form of local compression and tension stresses, is converted into thermal energy, leading to the increment in the temperature and creation of damage and/or the destruction of the cells.

Figure 4A:
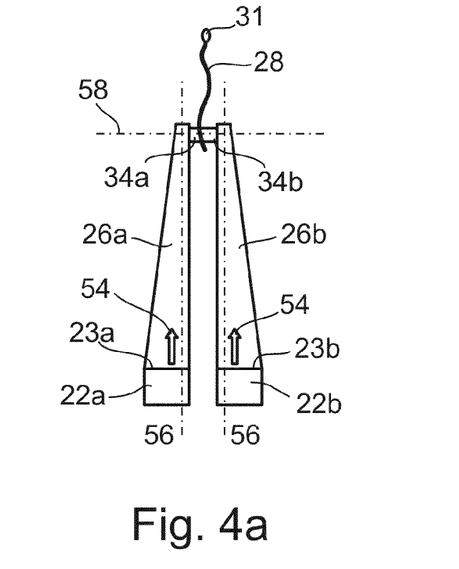
FIGS. 4a-b are schematic illustrations of a device for treating unwanted hair in a preferred embodiment in which the propagation direction of the acoustic waves, while entering the wave condenser is generally perpendicular to the longitudinal axis of the hair.
Figure 4B:
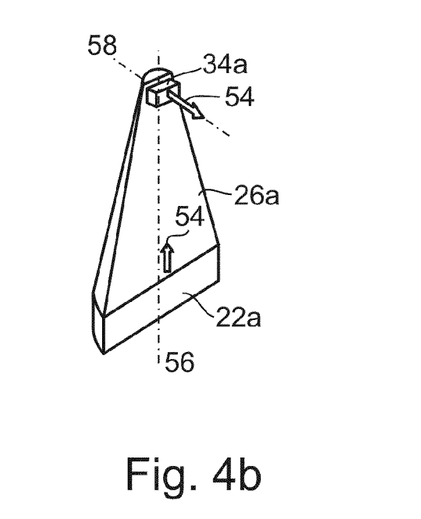

Reference is now made to FIGS. 4*a-b* which are schematic illustrations of device 20 in a particular configuration which is preferably used in the perpendicular orientation embodiment. In this embodiment, transducer 22 comprises a first part 22*a* and a second part 22*b*, each having one or more active elements (respectively designated 23*a* and 23*b*), planar or non-planar, as further detailed hereinabove. Focusing element 26 also comprises a first part 26*a* and a second part 26*b*, where first 26*a* and second 26*b* parts of focusing element 26 respectively couple first 22*a* and second 22*b* parts of transducer 22 with first 34*a* and second 34*b* parts of chamber 34 of wave condenser 24. The coupling between the first parts of transducer 22, element 26 and condenser 24 is isometrically illustrated in FIG. 4*b*.

Once hair shaft 28 is gripped between parts 34*a* and 34*b*, transducer 22 is activated and a wave front 54 of an acoustic wave begins to propagate from active elements 23 generally parallel to a longitudinal axis 56 defined by the, shape of focusing element 26. Focusing element 26 focuses the acoustic wave onto condenser 24, such that wave front 54 continues to propagate within condenser 24, generally parallel to an axis 58 which, can be, for example, symmetry axis 41. According to the presently preferred embodiment of the invention axis 58 is substantially perpendicular to axis 56 and to hair shaft 28. If desired, the inclined orientation embodiment can be employed, in which case, axis 58 is inclined to axis 56 by a predetermined angle.

Focusing element 26 preferably comprises a tapered housing, characterized by a wider cross-sectional area, D, and a narrower cross-sectional area, d. The height of the housing preferably equals a half-integer number of wavelengths of the acoustic waves (e.g., one half of wavelength). It is to be understood that the acoustic energy concentrator does not have to be cylindrically symmetrical. Focusing element 26 can be made of any material capable of reflecting acoustic waves. Representative examples for suitable materials include, without limitation, metal (e.g., aluminum) and polymers which typically used in ultrasound devices (e.g., polyurethanes).

The wider cross sectional area D of focusing element 26 is preferably from about 1 mm to about 20 mm, more preferably from about 4 mm to about 8 mm. The narrower cross-sectional area d is preferably from about 0.5 mm to about 5 mm, more preferably from 1 mm to about 3 mm. The profile of the tapered housing can have one or more characteristic angles, preferably following an exponential form, which effectively concentrate the acoustic energy to a small volume with minimal energy losses.

FIGS. 5*a-d* are schematic illustrations of different possible shapes for the tapered housing of focusing element 26, according to various exemplary embodiments of the present invention. Hence, the tapered housing can have a stepped profile (FIG. 5*a*) having a wider cylindrical part and a narrower cylindrical part. The height of each part is preferably about one quarter of a wavelength of the acoustic waves. In this embodiment magnification factor is given by the ratio D/d.

Figure 5A:
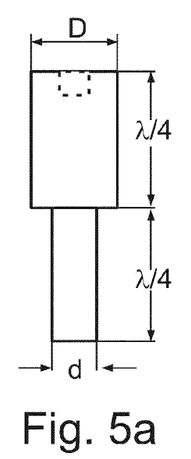
FIGS. 5a-d are schematic illustrations of different possible shapes for a tapered housing of a focusing element, according to various exemplary embodiments of the present invention.
Figure 5B:
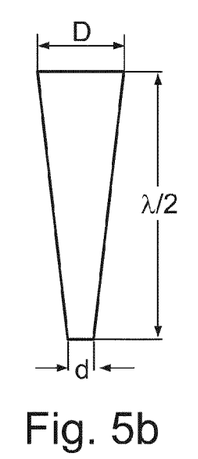

In another embodiment, shown in FIG. 5*b*, the tapered housing has a linear profile (e.g., a truncated cone).

Figure 5C:
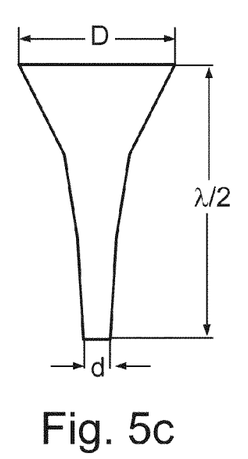

In an additional embodiment, shown in FIG. 5*c*, the housing has an exponential profile. Such design offers higher magnification factors as compared to the linear profile. Its shape makes it more difficult to manufacture but its length coupled with a small diameter at the working end makes this design particularly suited to micro applications.

Figure 5D:
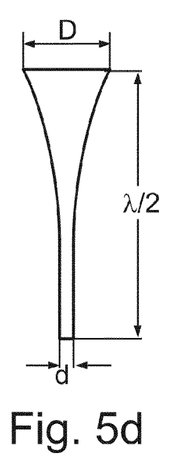

In another embodiment, shown in FIG. 5*d*, the tapered housing has a segmented linear profile, having a plurality of linear segments. For example, in this embodiment the housing can be made of a plurality of truncated cone each having a smaller opening angle. The opening angles can be selected so as to approximate an exponential profile.

Figure 6A:
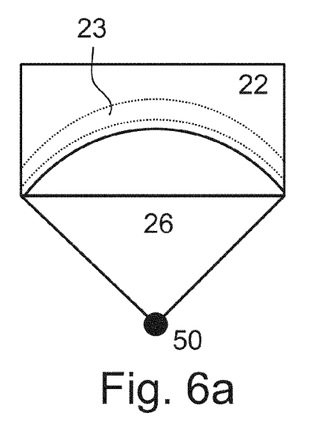
FIGS. 6a-b are schematic illustrations of an acoustic waves transducer and a focusing element, according to various exemplary embodiments of the invention.
Figure 6B:
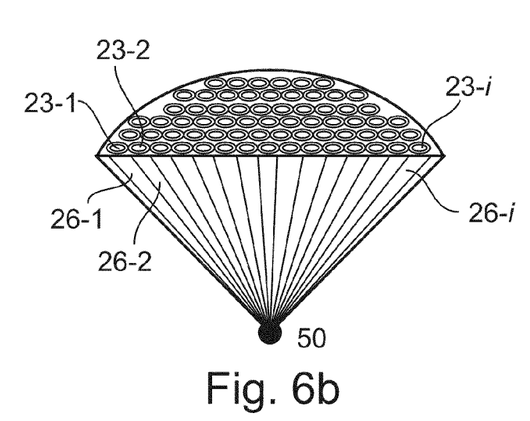

FIGS. 6*a-b* are schematic illustrations of transducer 22 and focusing element 26 in the preferred embodiment in which focusing element 26 comprises a tapered housing. It is to be understood that although the illustrations in FIGS. 6*a-b* are directed at a linear profile, other profiles are not excluded from the scope of the present invention. Hence, according to the presently preferred embodiment of the invention active element 23 of transducer 22 has a spherical shape. The acoustic waves are generated by active element 23, enter focusing element 26 which focus them and generates a small volume 50 of maximal energy density within condenser 24 (not shown FIGS. 6*a-b*). FIG. 6*b* is a schematic illustration of the preferred embodiment in which transducer 22 comprises n active elements, designated in FIG. 6*b* by numerals 23-i (i=1, 2, . . . , n). In this embodiment, device 20 preferably comprises n focusing elements 26-i (i=1, 2, . . . , n), such that each individual active element is connected to a respective individual focusing element whereby all the focusing elements preferably focus the waves to volume 50.

Referring now again to FIG. 2, in various exemplary embodiments of the invention device 20 comprises a drive mechanism 48 for imparting a motion of wave condenser 24 and, optionally and preferably, of focusing element 26 and/or transducer 22, relative to the hair. Drive mechanism 48 can be utilized, for example, for gripping of hair shaft 28.

Drive mechanism 48 can be any known mechanism which can impart the desired motion. Typically, but not obligatorily, drive mechanism 48 utilizes an electrical motor 47 and a suitable transmission 49. Drive mechanism 48 can impart more than one type of motion. For example, in various exemplary embodiments of the invention drive mechanism 48 impart a rotary motion so as to periodically split and reassemble condenser 24, focusing element 26 and/or transducer 22 as further detailed hereinabove. Alternatively or additionally, drive mechanism 48 can impart a reciprocal linear motion to condenser 24 along the skin thereby to repeat the treatment to more than one hair and more than one time to each hair.

Figure 7A:
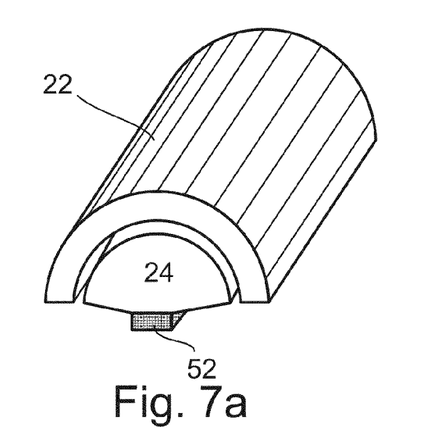
FIGS. 7a-c are schematic illustrations of a device for treating unwanted hair, which comprises a hair capturer, according to various exemplary embodiments of the invention.
Figure 7B:
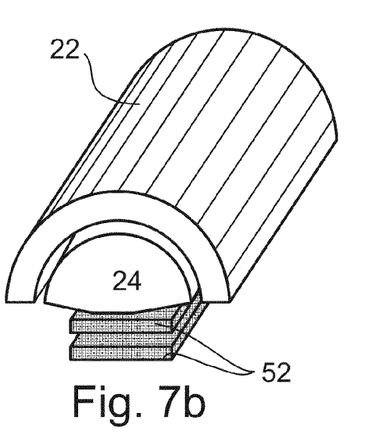
Figure 7C:
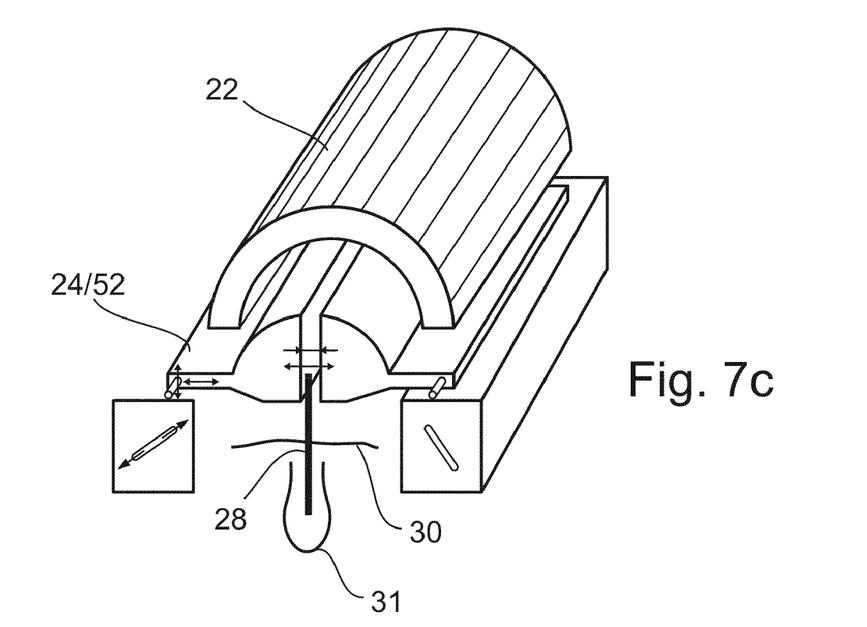

Reference is now made to FIGS. 7*a-c*, which are schematic illustration of device 20 in accordance with additional embodiments of the present invention. Device preferably comprises a hair capturer 52 for capturing the hair. Many types of hair capturers, disposable as well as reusable are contemplated. Typical hair capturers are those being utilized in epilation devices, e.g., a brush (FIG. 7*a*), a net (FIG. 7*b*) and a clamp (FIG. 7*c*). Other types of hair capturers as well as combinations between two or more types are also contemplated. Additionally, condenser 24 can serve as a hair capturer, as shown in the representative example of FIG. 7*c*. In any event, hair capturer 52 is preferably actuated by drive mechanism 48 (not shown in FIGS. 7*a-c*) which imparts hair capturer 52 with a rotary and/or reciprocal linear motion as further detailed hereinabove.

In the embodiments shown in FIGS. 7*a-c*, transducer 22 has a shape of a cylindrical cut, where the active element is concaved hence allows the focusing of the acoustic waves into condenser 24. According to the presently preferred embodiment of the invention, condenser 24 has a shape of a portion (e.g., about one half) of a cylinder. The acoustic waves bounce back and forth between the concaved surface of transducer 22 and the symmetry axis of the cylinder, while the hair shaft is gripped by hair capturer 52 below the focal plane of transducer 22. Hair capturer 52 preferably lubricates the hair shaft with an ultrasound transmission gel during the capturing so as to enhance the acoustical contact between capturer 52 and the hair shaft. The ultrasound transmission gel can be partially or fully adhesive. Capturer 52 can incorporate grooves and/or holes through which ultrasound transmission gel or any other compound can be pushed towards the hair shaft surface. The presence of gel also enlarges the contact area and thereby improves the acoustic power transfer to the hair. Capturer 52 can also be used for pulling the hair subsequently to the destruction of the cells, as further detailed hereinabove.

It is expected that during the life of this patent many relevant instrumentations for generating focusing and condensing acoustic waves will be developed, and the scopes of the terms transducer, condenser and focusing element are intended to include all such new technologies a priori.

Additional objects, advantages and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions illustrate the invention in a non limiting fashion.

Computational Model

Figure 8:
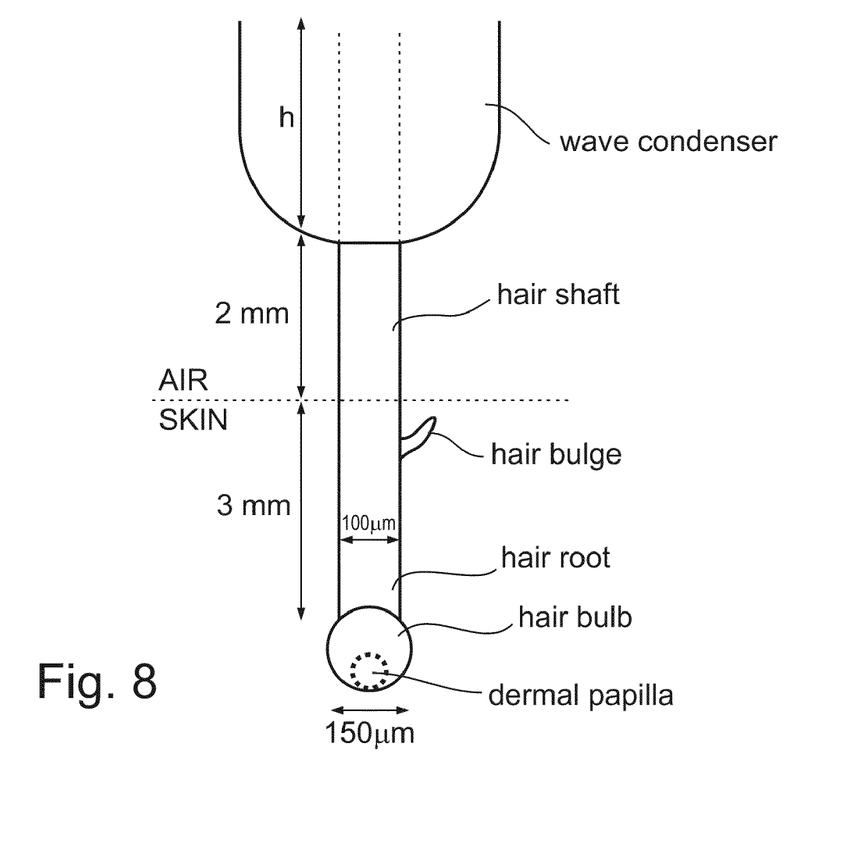
FIG. 8 is an illustration of a simplified model of the geometry of the hair, according to various exemplary embodiments of the invention.

FIG. 8 is a schematic illustration of a simplified model of the geometry of the hair, which include three well distinguished regions: (i) the hair shaft above and below the skin surface, (ii) the hair bulb which comprises the dermal papilla and the germinal matrix, and (iii) the hair bulge, which is a part of the follicle and located near the hair shaft between the skin surface and the hair bulb. The hair shaft has a substantially smooth and extended structure and is located within the air, or the soft tissues which have distinctly different acoustic impedance. The hair shaft presents a good system for guiding an acoustic energy from the top end to the hair bulge and the entry point into the hair bulb.

The geometry of the hair bulb and hair bulge considerably differs from the geometry of the hair shaft. Multitude of the curved segments having different acoustic impedance values present ideal structure for multiple reflections of acoustic wave. The high absorbance of the hair bulb and hair bulge material (about 1 dB/mm at a frequency of about 1 MHz) results in intensive local energy release and transient temperature rise at the hair bulb and hair bulge regions.

Calculations performed by the Inventors of the present invention show that in order to bring the temperature of the hair bulb and hair bulge from normal body temperature to about 70° C. within about 10-100 milliseconds, absorption of ultrasound power at a rate of less than 10 milliwatts is required. The ultrasound absorption in the hair bulb and hair bulge at about 1 MHz is estimated to be about 10-20% of the ultrasound energy transmitted into it, while the remaining portion of energy is transmitted into the surrounding tissue. Therefore, the required ultrasound power that needs be injected into the hair bulb and hair bulge is less than about 50-100 milliwatts.

A hair shaft of 5 mm in length (from the tip of the wave condenser 24 to the hair bulb), absorbs about 1 dB/mm at a frequency of about 1 MHz. Thus, an ultrasound power of less than about 150-300 milliwatts injected for about 10-100 milliseconds into the hair shaft can result in a temperature of about 70° C. in the hair bulb and hair bulge. As stated, such temperature can destroy the cells in the follicle. A power level of 150-300 milliwatts, although small in magnitude, is rather large in density. Specifically as the hair shaft cross-sectional area is about 0.00008 cm², a power level of 150-300 milliwatts corresponds to a power density of about 2000-4000 watts/cm².

The wave condenser, as stated, typically grips several millimeters of hair shaft (from h≈2 mm. to h≈5 mm), corresponding to a total area of a few tenths of square millimeters to a few square millimeters (0.006 cm² for h≈2 mm and 0.016 cm² for h≈5 mm). By acoustically coupling between the hair shaft and the acoustic waves, the entire area the hair shaft along the coupling length, h, can be exploited for collecting the acoustic energy. A power density of 2000-4000 watts/cm² can therefore be collected within the hair shaft using a wave condenser and an ultrasound transducer which generates from about 10 watts/cm² to about 55 watts/cm² of power density.

The longitudinal vibration amplitude ϵ of the hair shaft (the longitudinal displacement of particle along the hair shaft), can be calculated by the following equation:

$$\varepsilon = \sqrt{\left(\frac{I}{2\pi^2 f^2 Z}\right)} \qquad \text{(EQ. 1)}$$

where I is the ultrasound density, Z is the acoustic impedance of the vibrating element, and f is the ultrasound frequency.

For a density I of 4000 watts/cm² (4×10⁷ watts/m²), a frequency f of 800 kHz, and an acoustical impedance of the hair shaft of 3.24×10⁶ kg/m²s, the vibration amplitude ϵ of the hair shaft near the wave condenser, according to Equation 1 above, is 0.99 μm. At any other point along the hair shaft towards the hair bulb, as well as at the hair bulb and hair bulge, ϵ is much less than 1 μm. For example, the ultrasound intensity at the distal end of the hair bulb is estimated to be about 5 times smaller than that at the hair shaft exit from the wave condenser, hence the vibration amplitude at this point is about 0.44 μm. This amplitude is too small to cause a mechanical depilation of the hair.

Note that in the above discussion a rather high power density value was used. Any lower intensity value results in smaller vibration amplitude. The vibration amplitude is inversely proportional to the ultrasound frequency. Experiments made by the Inventors of the present invention showed that at an ultrasound frequency of 250 kHz, under the same operating conditions (I=4000 watt/cm$^2$ and Z=3.24×10$^6$ kg/m$^2$s), the temperature of the hair bulb did not go beyond 40° C. Borderline effects of hyperthermia or any other thermal damage are expected to occur at this low frequency level. However, even at this frequency limit value, the vibration amplitude at the distal end of the hair bulb is computed to be only 1.4 µm, which is still too small to cause a mechanical depilation of the hair.

Irradiating Hair Shafts by Ultrasound Waves

Experiment 1

A prototype wave condenser was built in accordance with a preferred embodiment of the present invention. The wave condenser was manufactured with a pore which was filled with ultrasound transmission gel. The diameter of the wave condenser was 8 mm and the dimensions of the pore were 1 mm in diameter and 5 mm in length.

A few human hair shafts were introduced into the condenser. An ultrasound transducer was assembled directly on the condenser, without intermediate focusing element. The ultrasound transducer was operated for about 0.1 second at a frequency of 1005 kHz and a power density of about 5.2 watts/cm$^2$ on its surface.

Figure 9:
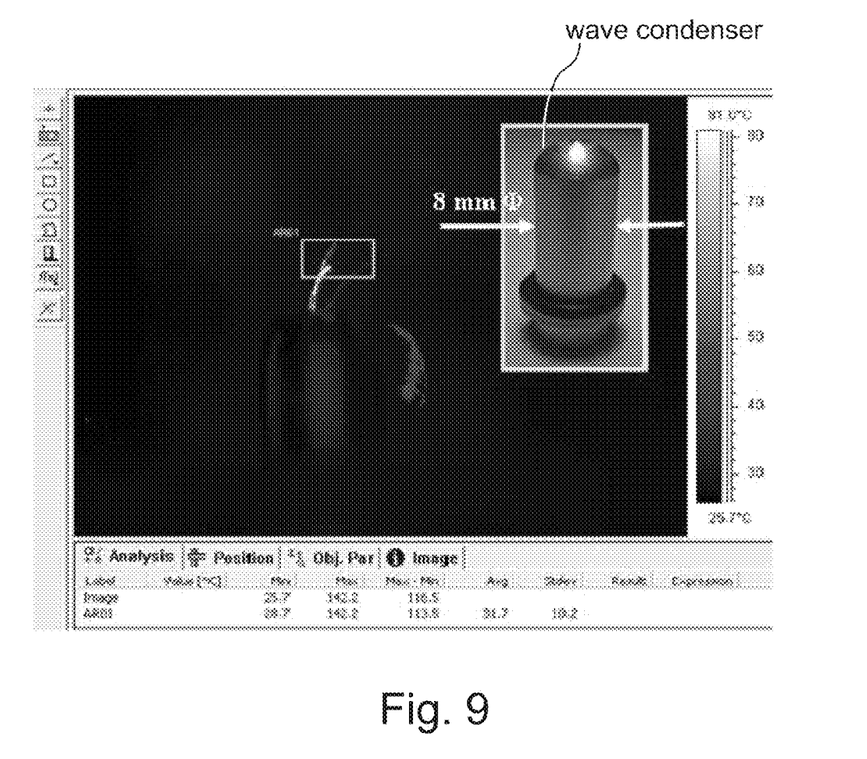
FIG. 9 is an infrared image of hair shafts treated by ultrasound waves, according to various exemplary embodiments of the invention.

FIG. 9 is an infrared image of the treated hair shafts. Also shown in FIG. 9 is an image of the wave condenser. As shown in FIG. 9, the acoustic waves successfully heated the hair shafts with the hot point at the distal end of the hair shaft acquiring a temperature of 142° C.

Experiment 2

Four human hair shafts were introduced into the wave condenser of Experiment 1. For each hair shaft, a different coupling length h was defined by a different insertion depth of the hair shaft into the wave condenser. The following coupling lengths were examined, h=2 mm, h=4 mm, h=6 mm and h=8 mm. The ultrasound frequency was 817 kHz, and the power density at the surface of the ultrasound transducer was set at two values: a lower density of about 1.2 watts/cm$^2$ and higher density of about 2.5 watts/cm$^2$.

Figure 10:
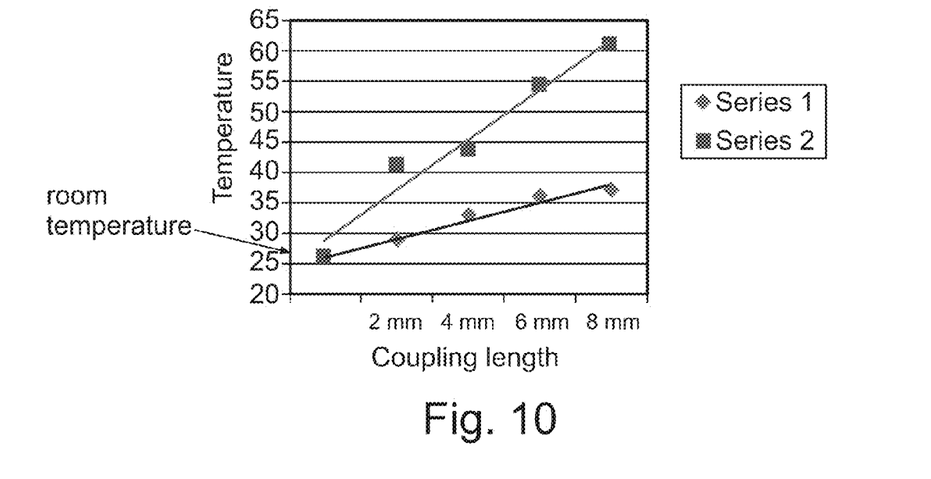
FIG. 10 shows the temperature of the hair shafts as a function of the coupling length.

FIG. 10 is a graph showing the temperature of the hair shafts as a function of the coupling length. As shown in FIG. 10, a close to linear increment of the hair shaft temperature with h was observed. This result is in agreement with the above model, because larger values of the coupling length correspond to higher levels of wave penetration into the hair shaft thereby to larger ultrasound energy propagation within the hair shaft.

Experiment 3

A human hair shaft with a hair follicle was inserted ex-vivo into rounded gel bulb, 6 mm in diameter which served as a wave condenser. The gel bulb was positioned directly on top of an ultrasound transducer, without a focusing element, with the hair bulb protruding into the air. To simulate the dermal tissue surrounding the hair bulb, a few millimeters of gel were applied on the protruding hair bulb. The ultrasound transducer was operated at a frequency 1005 kHz, providing, at its surface, about 3 watts/m$^2$. The duration of treatment was 0.1 second.

Figure 11:
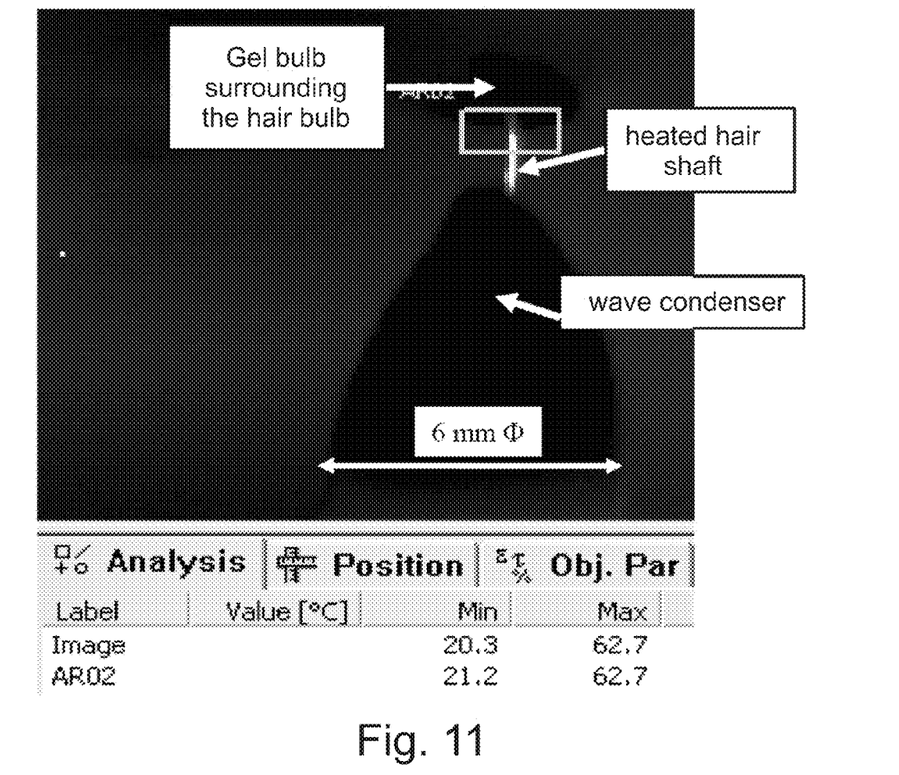
FIG. 11 is an infrared image of hair shafts and hair bulbs treated by ultrasound waves, according to various exemplary embodiments of the invention.

FIG. 11 is an infrared image of the treated hair shaft. Shown in FIG. 11, is a 2 mm section of the hair shaft between the wave condenser and the gel bulb which was heated by the ultrasound waves to a temperature of about 62° C.

Figure 12A:
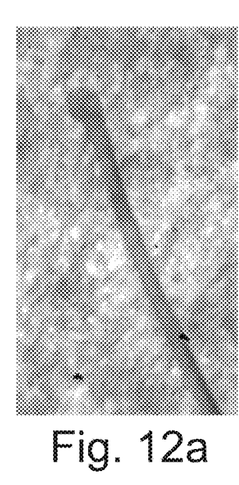
FIGS. 12a-c are optical microscope images comparing hair bulbs before (FIG. 12a) and after (FIGS. 12b-c) treatment by the ultrasound waves.
Figure 12B:
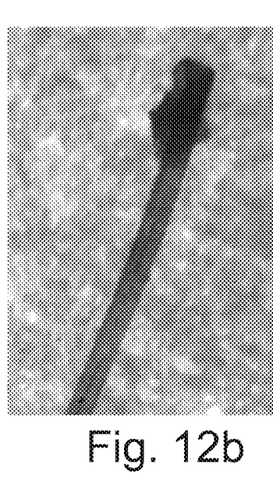
Figure 12C:
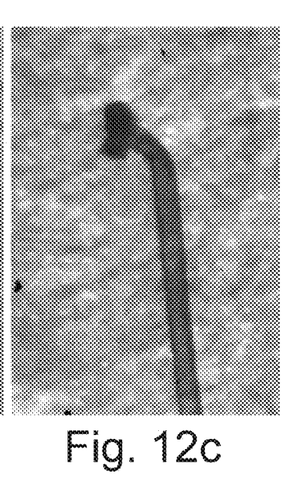

FIG. 12c are optical microscope images comparing hair bulbs before (FIG. 12a) and after (FIGS. 12b-c) treatment by the ultrasound waves. As shown in FIGS. 12b-c the energy of the ultrasound waves, condensed by the ultrasound wave condenser and transmitted through the hair shaft, was absorbed by the hair bulb located within a thick gel bulb. The absorption of energy caused a temperature increase which was followed by a complete disfigurement of the hair bulb.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of treating unwanted hair, comprising transmitting acoustic waves at a frequency of from about 150 kHz to about 1300 kHz through the hair so as to generate heat at a follicle, a dermal papilla, a hair bulge and/or a germinal matrix of the hair, said heat being in itself sufficient to damage or destroy said follicle, said dermal papilla, said hair bulge and/or said germinal matrix.

2. The method of claim 1, further comprising using a wave condenser for condensing said acoustic waves, prior to said transmitting of said acoustic waves through the hair.

3. The method of claim 1, further comprising gripping the hair prior to transmitting of said acoustic waves so as to enhance acoustic coupling between the hair and said acoustic waves.

4. The method of claim 3, wherein said gripping is by a wave condenser operative to grip said hair and the method further comprises using said wave condenser for condensing said acoustic waves, prior to said transmitting of said acoustic waves through the hair, wherein said gripping comprises positioning the hair and/or said wave condenser such that a propagation direction of said acoustic waves while entering said wave condenser is generally parallel to a longitudinal axis of the hair.

5. The method of claim 3, wherein said gripping is by a wave condenser operative to grip said hair and the method further comprises using said wave condenser for condensing said acoustic waves, prior to said transmitting of said acoustic waves through the hair, wherein said gripping comprises positioning the hair and/or said wave condenser such that a propagation direction of said acoustic waves while entering said wave condenser is generally perpendicular to a longitudinal axis of the hair.

6. The method of claim 3, wherein said gripping is by a wave condenser operative to grip said hair and the method further comprises using said wave condenser for condensing said acoustic waves, prior to said transmitting of said acoustic waves through the hair, wherein said gripping comprises positioning the hair and/or said wave condenser such that a propagation direction of said acoustic waves while entering said wave condenser is generally inclined to a longitudinal axis of the hair.

7. The method of claim 3, further comprising pulling the hair so as to effect a detachment of the hair.

8. The method of claim 3, wherein said acoustic coupling is characterized by a coupling length selected such that said heat at said follicle, said dermal papilla, said hair bulge and/or said germinal matrix results in a temperature increment of at least 20 degrees centigrade.

9. The method of claim 1, wherein at least one of: a frequency, a power density and duration of transmission of said acoustic waves is selected so as to minimize vibrations of the hair.

10. The method of claim 1, wherein at least one of: a frequency, a power density and duration of transmission of said acoustic waves is selected such that said generation of said heat is such that said heat at said follicle, said dermal papilla, said hair bulge and/or said germinal matrix results in a temperature increment of at least 20 degrees centigrade.

11. The method of claim 10, wherein said frequency is an off-resonance frequency.

12. The method of claim 10, wherein said acoustic waves comprise ultrasound waves.

13. The method of claim 12, wherein said ultrasound waves are at a frequency of at least 500 kHz. comprise ultrasound waves.

14. A device for treating unwanted hair protruding from a skin, the device comprising:
a transducer for generating acoustic waves at a frequency of from about 150 kHz to about 1300 kHz; and
a wave condenser, for gripping the hair to establish acoustic coupling between said acoustic waves and the hair in a manner such that said acoustic waves are condensed, transmitted through the hair past the skin and generate heat at a follicle, a dermal papilla, a hair bulge and/or a germinal matrix of the hair;
said heat being in itself sufficient to damage or destroy said follicle, said dermal papilla, said hair bulge and/or said germinal matrix.

15. The device of claim 14, wherein said wave condenser is designed and constructed such that a propagation direction of said acoustic waves while entering said wave condenser is generally parallel to a longitudinal axis of the hair.

16. The device of claim 14, wherein said wave condenser is designed and constructed such that a propagation direction of said acoustic waves while entering said wave condenser is generally perpendicular to a longitudinal axis of the hair.

17. The device of claim 14, wherein said wave condenser is designed and constructed such that a propagation direction of said acoustic waves while entering said wave condenser is generally inclined to a longitudinal axis of the hair.

18. The device of claim 14, wherein at least one of: a frequency, a power density and duration of transmission of said acoustic waves is selected so as to minimize vibrations of the hair.

19. The device of claim 14, wherein at least one of: a frequency, a power density and a duration of transmission of said acoustic waves is selected such that said heat at said follicle, said dermal papilla, said hair bulge and/or said germinal matrix results in a temperature increment of at least 20 degrees centigrade.

20. The device of claim 19, wherein said frequency is an off-resonance frequency.

21. The device of claim 19, wherein said transducer is an ultrasound transducer generating ultrasound waves.

22. The device of claim 21, wherein said wave condenser comprises a chamber configured to receive the hair such that energy of said acoustic waves is transferred to the hair from a plurality of directions.

23. The device of claim 21, wherein said ultrasound waves are at a frequency of at least 500 kHz.

24. The device of claim 14, further comprising a focusing element coupling said transducer and said wave condenser, said focusing element being designed and constructed to focus said acoustic waves into said wave condenser.

25. A device for treating unwanted hair protruding from a skin, the device comprising:
a transducer for generating acoustic waves; and
a wave condenser, for gripping the hair to establish acoustic coupling between said acoustic waves and the hair in a manner such that said acoustic waves are condensed, transmitted through the hair past the skin and increase a temperature at a follicle, a dermal papilla, a hair bulge and/or a germinal matrix of the hair by at least 20 degrees centigrade.

26. A method of treating unwanted hair, comprising transmitting acoustic waves through the hair so as to so as to generate heat at a follicle, a dermal papilla, a hair bulge and/or a germinal matrix of the hair, wherein at least one of: a frequency, a power density and duration of transmission of said acoustic waves is selected such that a characteristic amplitude of longitudinal vibrations of the hair is below 10 μm.

27. A device for treating unwanted hair protruding from a skin, the device comprising:
a transducer for generating acoustic waves; and
a wave condenser, for gripping the hair to establish acoustic coupling between said acoustic waves and the hair in a manner such that said acoustic waves are condensed, transmitted through the hair past the skin and generate heat at a follicle, a dermal papilla, a hair bulge and/or a germinal matrix of the hair;
wherein at least one of: a frequency, a power density and duration of transmission of said acoustic waves is selected such that a characteristic amplitude of longitudinal vibrations of the hair is below 10 μm.

* * * * *